United States Patent
Hecht et al.

(10) Patent No.: US 9,846,844 B2
(45) Date of Patent: Dec. 19, 2017

(54) METHOD AND SYSTEM FOR QUANTITATIVELY EVALUATING THE CONFIDENCE IN INFORMATION RECEIVED FROM A USER BASED ON COGNITIVE BEHAVIOR

(71) Applicant: International Business Machines Corporation, Armonk, NY (US)

(72) Inventors: Jae-Lyn Hecht, Boston, MA (US); James R. Kozloski, New Fairfield, CT (US); Fang Lu, Billerica, MA (US); Azadeh Salehi, Pepperell, MA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/951,636

(22) Filed: Nov. 25, 2015

(65) Prior Publication Data
US 2017/0147934 A1    May 25, 2017

(51) Int. Cl.
*G06F 17/00*    (2006.01)
*G06N 7/00*     (2006.01)
*G06N 99/00*    (2010.01)
*G06F 19/00*    (2011.01)

(52) U.S. Cl.
CPC ........... *G06N 7/005* (2013.01); *G06F 19/345* (2013.01); *G06N 99/005* (2013.01)

(58) Field of Classification Search
CPC ....................................................... G09B 7/00
USPC ............................................. 706/12, 45, 62
See application file for complete search history.

(56) References Cited

U.S. PATENT DOCUMENTS

| | | |
|---|---|---|
| 5,983,129 A | 11/1999 | Cowan |
| 7,207,938 B2 | 4/2007 | Hursh |
| 7,403,814 B2 | 7/2008 | Cox |
| 7,761,144 B2 | 7/2010 | Cox |
| 8,473,043 B1 | 6/2013 | Modarres |
| 2006/0200350 A1 | 9/2006 | Attwater |
| 2013/0177883 A1 | 7/2013 | Barnehama |
| 2013/0266925 A1* | 10/2013 | Nunamaker, Jr. ... G06N 99/005 434/362 |
| 2014/0371549 A1* | 12/2014 | Yaffe-Ermoza ...... A61B 5/6806 600/301 |
| 2015/0052089 A1* | 2/2015 | Kozloski ................ G06N 99/00 706/12 |
| 2016/0196265 A1* | 7/2016 | Allen ................. G06F 17/3053 707/734 |
| 2017/0124475 A1* | 5/2017 | Anderson .............. G06N 7/005 |

* cited by examiner

Primary Examiner — David Vincent
(74) Attorney, Agent, or Firm — Cantor Colburn LLP

(57) ABSTRACT

A computer-implemented method of evaluating information confidence based on a cognitive trait of a user, is provided, the method including receiving information from a user as an answer to a question in an active learning question and answer system; monitoring a user for a cognitive behavior indicator when the user is providing the information; determining a cognitive trait based on the cognitive behavior indicator; determining a quantified level of information confidence for the information based on the cognitive trait; and annotating the information with the cognitive trait and the quantified level of information confidence. A system and a computer program product for evaluating information confidence based on a cognitive behavior of a user are also provided.

17 Claims, 5 Drawing Sheets

METHOD AND SYSTEM FOR QUANTITATIVELY EVALUATING THE CONFIDENCE IN INFORMATION RECEIVED FROM A USER BASED ON COGNITIVE BEHAVIOR

BACKGROUND

The present invention relates to a method and system for evaluating the confidence in information received from a user, and more specifically, to using cognitive behavior indicators of the user when providing information as an answer to a question to identify a cognitive trait and to determine a quantified level of confidence for the information based on the cognitive trait.

In active learning question and answer systems, such as those used in and for internet and other database search engines, a semi-supervised machine utilizes an active learning algorithm in which a user is interactively queried to obtain desired outputs as new data points. The information input by a user in response to an automated query is used to improve the relevance and quality of the results generated by the system.

Manually labeling data points in the active learning system can be quite costly and time-consuming. The active learning algorithms generate a query to a user or a teacher to provide such labels. However, the resulting label information provided by the user or a teacher may be uninformative and/or inaccurate due to the influence of external stimuli such as stress, medical factors, ambient noise, other distractions and/or other influences which may affect the accuracy and/or relevance of the user's response at the time the information is provided. The inaccuracy or lack of relevance of the user's response may then in turn be inaccurate and/or irrelevant for subsequent users of the system in the future.

SUMMARY

According to an embodiment, a computer-implemented method of evaluating information confidence based on a cognitive trait of a user is provided. The method includes receiving information from a user as an answer to a question in an active learning question and answer system; monitoring the user for a cognitive behavior indicator when the user is providing the information; determining a cognitive trait based on the cognitive behavior indicator; determining a quantified level of information confidence for the information based on the cognitive trait; and annotating the information with the cognitive trait and the quantified level of information confidence.

According to another embodiment, a system for evaluating information confidence based on a cognitive trait of a user is provided. The system includes a sensor to detect a cognitive behavior indicator of a user; a memory; a processor communicatively coupled to the memory and the sensor, where the processor is configured to perform: receiving information from a user as an answer to a question in an active learning question and answer system; monitoring the user for a cognitive behavior indicator detected by the sensor when the user is providing the information; determining a cognitive trait based on the cognitive behavior indicator; determining a quantified level of information confidence for the information based on the cognitive trait; and annotating the information with the cognitive trait and the quantified level of information confidence.

According to another embodiment, a computer program product for evaluating information confidence based on a cognitive trait of a user is provided. The computer program product includes a computer readable storage medium having a computer readable program code embodied therewith, the computer readable program code configured to perform receiving information from a user as an answer to a question in an active learning question and answer system; monitoring the user for a cognitive behavior indicator detected by a sensor when the user is providing the information; determining a cognitive trait based on the cognitive behavior indicator; determining a quantified level of information confidence for the information based on the cognitive trait; and annotating the information with the cognitive trait and the quantified level of information confidence.

BRIEF DESCRIPTION OF THE DRAWINGS

The accompanying figures wherein reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

Figure 1:
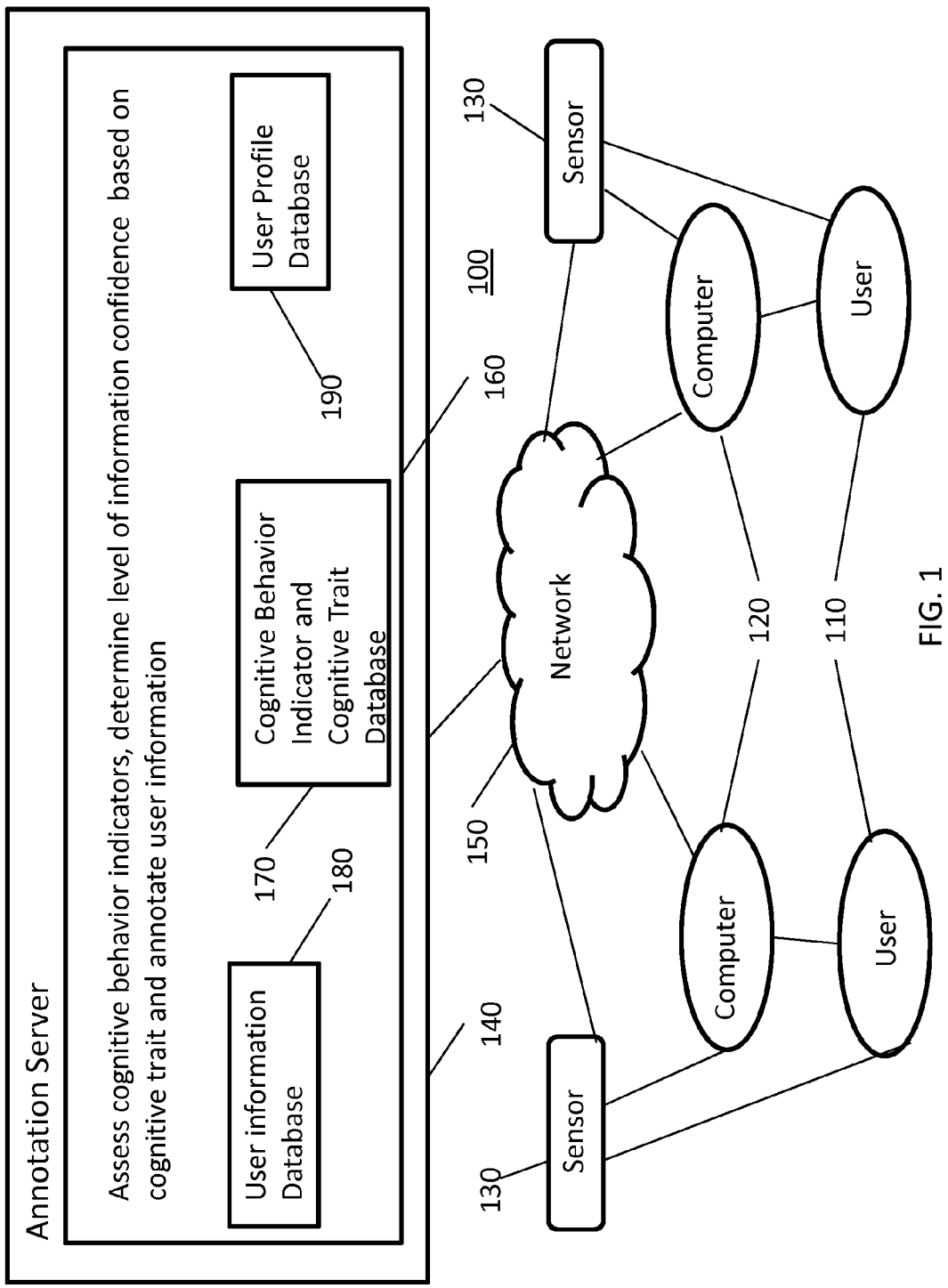
FIG. 1 is a functional diagram illustrating an exemplary operating embodiment.

With reference now to FIG. 1, a functional diagram illustrating an exemplary embodiment of an operating system 100 is shown in which at least one user 110 using a computer 120 is prompted to answer a question in an active learning question and answer system, e.g., to provide a label for an identified data point. A sensor 130 monitors the user while inputting the information to detect one or more cognitive behavior indicators. An annotation server 140 is communicatively coupled over a network 150 to the user's computer 120. The annotation server 140 includes a cognitive behavior assessment, information confidence rating and annotating information software module 160 for determining a cognitive trait based on the cognitive behavior indicator, determining a quantified level of information confidence for the information based on the cognitive trait and annotating the information with the cognitive trait and the quantified level of information confidence.

The annotation server 140 may include one or storage areas or databases for recording information. Although for clarity these databases are shown as separate storage areas or databases it is important to note that only a single storage area or database may be used. The databases shown are a cognitive behavior indicator database 170, a user information database 180 and a user profile database 190.

Information provided by the user in response to the automated query is stored in the user information database 180. The information provided by the user is annotated with the cognitive trait and quantified level of information confidence generated by the annotation server 140. The annotation may also include the raw data from which the cognitive trait was extracted, and information about the cognitive trait extraction method, such as model description, model version number, and other information concerning model provenance. Subsequent accessing of the annotation may include recalculating the cognitive trait and quantified level of information confidence if the model, model version number, or other information about model provenance has been revised since the most recently calculated cognitive trait.

The cognitive behavior indicator and cognitive trait database 170 determines a cognitive trait based on the cognitive behavior indicator detected from the user and determines a quantified level of information confidence for the information based on the cognitive trait, as discussed further below.

User profile information is stored in the user profile database 190. User profile information may include information such as the user's profession, areas of knowledge or expertise, physical health, proficient languages, gender, age, work title and years of experience. User profile information may also be annotated with the cognitive trait information to determine the quantified level of information confidence for the information.

The operating system 100 may be used to obtain information and cognitive behavior indicators of multiple users 110. The software module 160 of annotation server 140 annotates the information, level of information confidence and cognitive behavior indicators and traits from multiple users to determine the quantified level of information confidence for the information and/or rank the results. The cognitive behavior indicators and traits may also be annotated with information from the user information database 180 and the user profile database 190 in order to rate the level of information confidence for the information and/or to rank the results of the multiple users based on the level of information confidence. In an embodiment, the software module 160 of annotation server 140 identifies matching patterns between multiple users with regard to one or more particular cognitive behavior indicators or traits and/or user profile information to improve the reliability of the quantified level of information confidence determined for the information by the confidence rating system.

In the active learning question and answer system, an active learning algorithm is used to interactively query the user in order to obtain desired outputs as new data points. The information input by the user in response to the automated query is used to improve the relevance and quality of the results generated by the system. The annotation server annotates the information received from the user with the cognitive behavior indicator detected when the information is being provided by the user with a cognitive trait to determine a quantified level of confidence for the information provided. The relative ratings of the relevance and accuracy of the information provided is then used by the active learning algorithm to rank the information received and thereby improve the accuracy and relevance of the results provided by the system.

A cognitive behavior indicator is a measurement which reflects whether the user may be influenced by external stimuli at the time the information is provided by the user. The sensor 130 detects one or more cognitive behavior indicators by performing a biometric measurement of the user at the time information is provided by the user. The cognitive behavior indicator is based on a biometric measurement of the behavior and/or the physiology of the user. In another embodiment, the cognitive behavior indicator is based on a measurement of other external stimuli in the vicinity of the user, such as ambient noise. Examples of cognitive behavior indicators include, but are not limited to, user eye tracking, user typing speed, user heart rate, user breathing rate, user blink frequency, user skin conductance, electroencephalogram information, user body temperature, user perspiration quantity, user blood pressure, user amount of time elapsed during information input or a combination of one or more of the foregoing.

The sensor 130 may be part of or embedded in the computer 120 itself or may be external to the computer. The sensor 130 may be in operative communication with the computer, the network, or both the computer and network 150. In an embodiment, the sensor 130 is a wearable device worn by the user.

The cognitive behavior indicator is annotated with information for cognitive traits related to the relative degree of focus or distraction of the user when information is being provided by the user. The associated information is rated according to the relative focus or distraction indicated by the cognitive trait to determine a quantified level of information confidence. Information associated with a cognitive trait related to a high degree of focus is rated higher than information associated with a cognitive trait related to a lower degree of focus or higher degree of distraction. In an embodiment, information that is annotated with a quantified level of information confidence is excluded from the information results used in the question and answer active learning system when the level of information confidence is below a designated threshold.

In an embodiment, feature extraction techniques are used to identify certain cognitive traits. Specifically, the reduction of a set of cognitive behavior indicators measured over some period of time to a set of feature nodes and vectors, corresponding to the cognitive behavior indicators' representations in the lower dimensional feature space, is used to identify the emergence of a certain cognitive trait over that period of time. The relationship of one feature node to other similar nodes through edges in a graph corresponds to the temporal order of transitions from one set of measures and the feature nodes and vectors to another. Some connected subgraphs of the feature nodes are herein referred to as a "cognitive trait".

Figure 2:
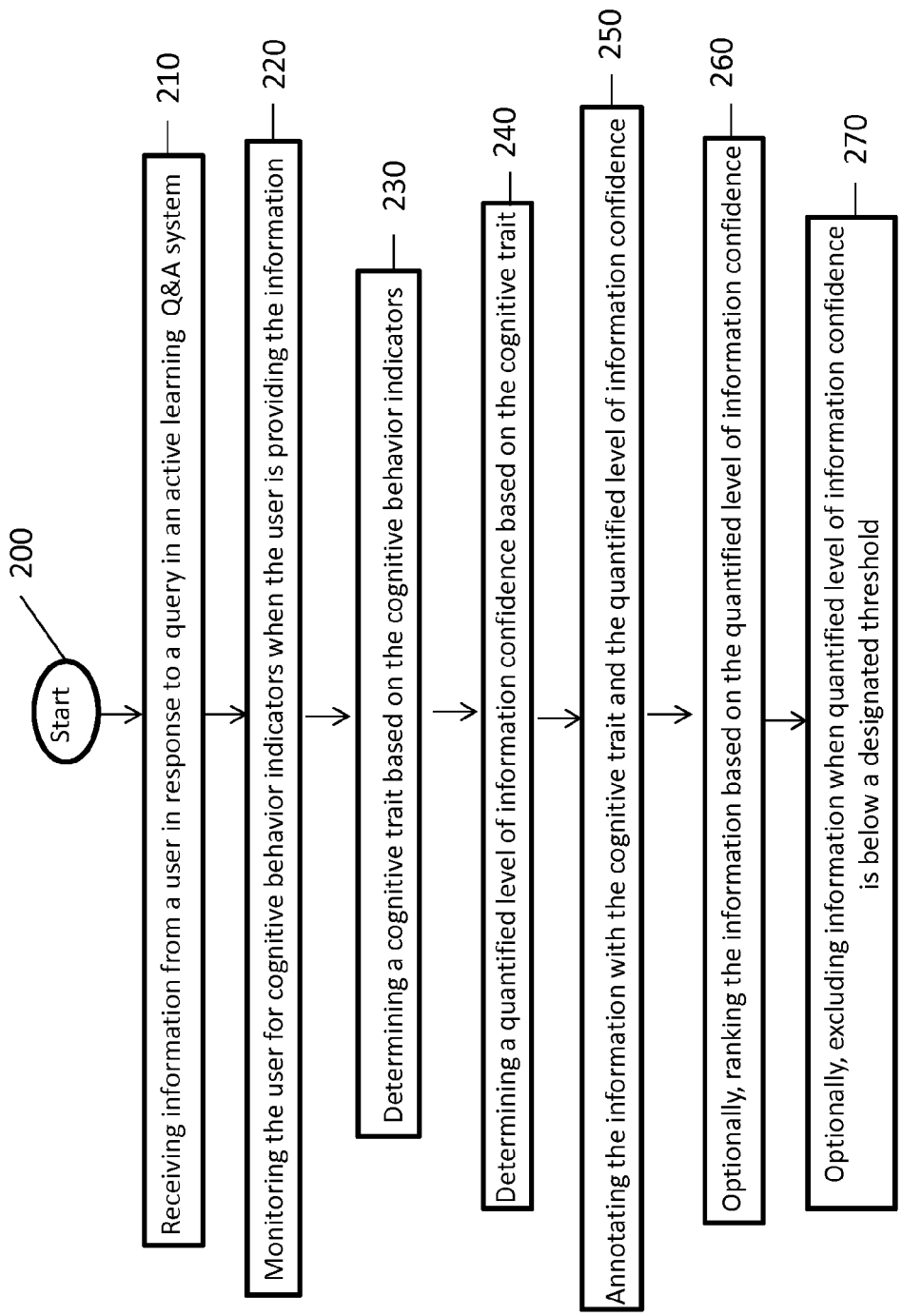
FIG. 2 is a flow chart of an exemplary embodiment of the computer-implemented method of evaluating information confidence based on a cognitive trait of a user.

Referring to FIG. 2, a flow chart of an exemplary embodiment of the computer-implemented method of evaluating information confidence based on a cognitive trait of a user is shown. The process begins in step 200 and immediately proceeds to step 210 to receive information from a user in response to a query from the active learning question and answer system. Next, in step 220, the user is monitored for one or more cognitive behavior indicators during the time that the user is providing the information. In step 230, a cognitive trait is identified based on the cognitive behaviors detected from the user. In step 240, a quantified level of information of confidence is determined based on the cognitive trait. In step 250, the information provided by the user is annotated with the cognitive trait and a quantified level of information of confidence. The information may also be annotated with user profile information. Optionally, in step 260, the information provided by multiple users is ranked according to the quantified level of information confidence assigned thereto. In optional step 270, information having a quantified level of information of confidence which is below a designated threshold is excluded from the information results.

Figure 3:
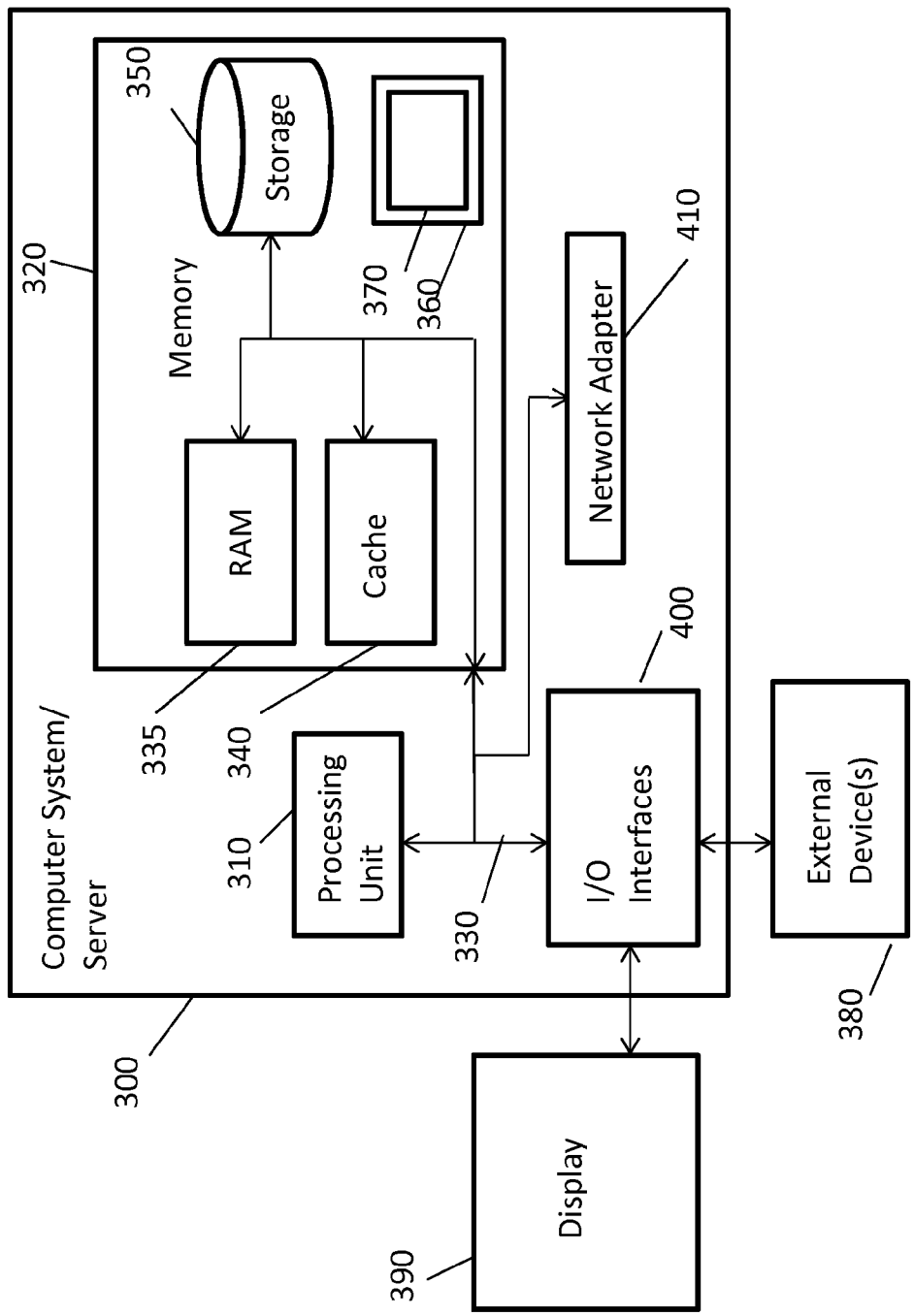
FIG. 3 is a block diagram illustrating an exemplary embodiment of an information processing system.

Referring to FIG. 3, a block diagram illustrating an information processing system is shown. The information processing system 300 is based upon a suitably configured processing system configured to implement one or more embodiments described herein, e.g., the cognitive behavior assessment, information confidence rating and annotating information software module 160 of FIG. 1. Any suitably configured processing system can be used as the information processing system 300 in the embodiments described herein. The components of the information processing system 300 can include, but are not limited to, one or more processors or processing units 310, a system memory 320 and a bus 330 that couples various system components including the system memory 320 to the processor 310.

The bus 330 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture bus, Micro Channel Architecture bus, Enhanced ISA bus, Video Electronics Standards Association local bus and Peripheral Component Interconnects bus.

Although not shown in FIG. 3, the system memory 320 includes the cognitive behavior assessment, information confidence rating and annotating information software module 160. The system memory 320 can also include computer system readable media in the form of volatile memory, such as random access memory ("RAM") 335 and/or cache memory 340. The information processing system 300 can further include other removable/non-removable, volatile/non-volatile computer system storage media. By way of example only, a storage system 350 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 330 by one or more data media interfaces. The memory 320 can include at least one program product having a set of program modules that are configured to carry out the functions of the embodiment described herein.

Program/utility 360, having a set of program modules 370, may be stored in memory 320 by way of example, and not limitation, as well as an operating system, one or more application programs, other program modules, and program data. Each of the operating system, one or more application programs, other program modules, and program data or some combination thereof, may include an implementation of a networking environment. Program modules 370 generally carry out the functions and/or methodologies of the embodiments described herein.

The information processing system 300 can also communicate with one or more external devices 380 such as a keyboard, a pointing device, a display 390, etc.; one or more devices that enable a user to interact with the information processing system 300; and/or any devices, e.g., network card, modem, etc., that enable computer system/server 300 to communicate with one or more other computing devices. Such communication can occur via I/O interfaces 400. Still yet, the information processing system 300 can communicate with one or more networks such as a local area network, a general wide area network, and/or a public network, e.g., the Internet, via network adapter 410. As depicted, the network adapter 410 communicates with the other components of information processing system 300 via the bus 330. Other hardware and/or software components can also be used in conjunction with the information processing system 300. Examples include, but are not limited to: microcode, device drivers, redundant processing units, external disk drive arrays, RAID systems, tape drives and data archival storage systems.

Certain aspects of the embodiments described herein may be a system, method, or computer program product. Accordingly, the embodiments described herein may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, embodiments described herein may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory, a read-only memory, an erasable programmable read-only memory, an optical fiber, a portable compact disc read-only memory, an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for the embodiments described herein may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems) and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 4:
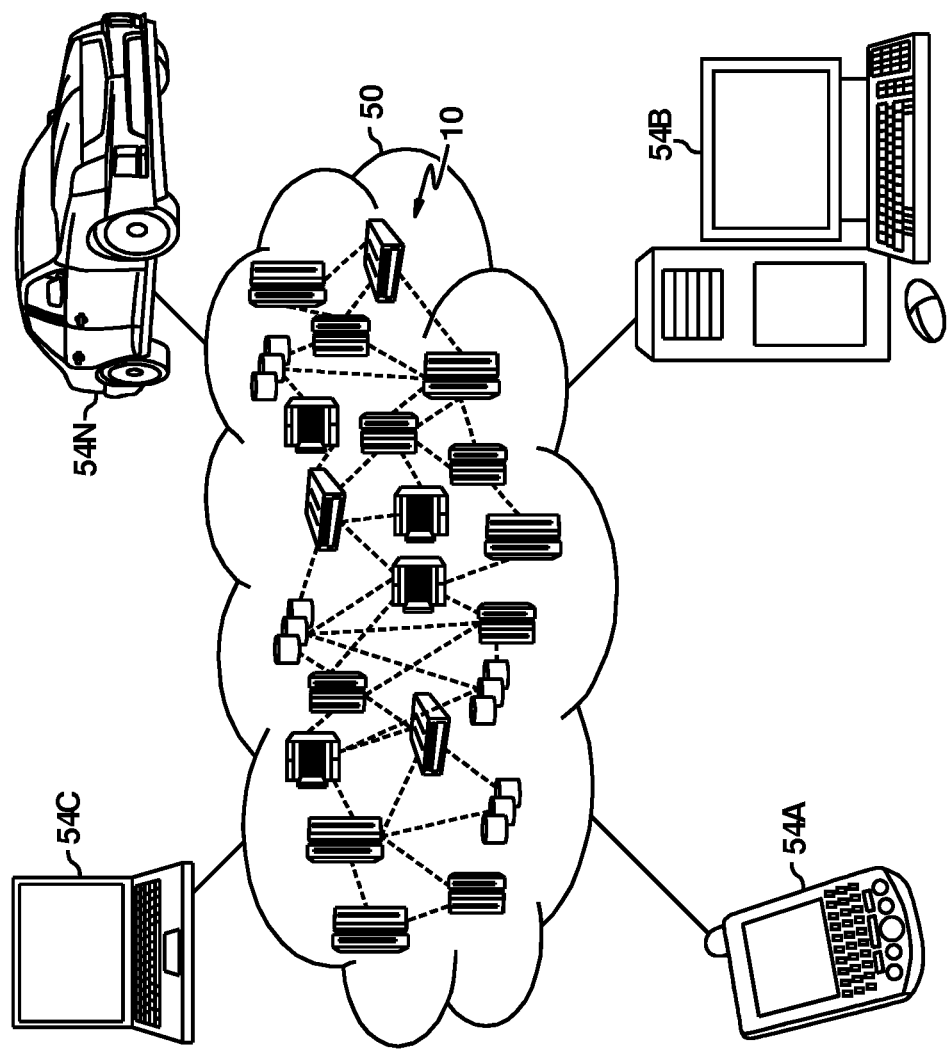
FIG. 4 is illustrative of a cloud computing environment.

Referring now to FIG. 4, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
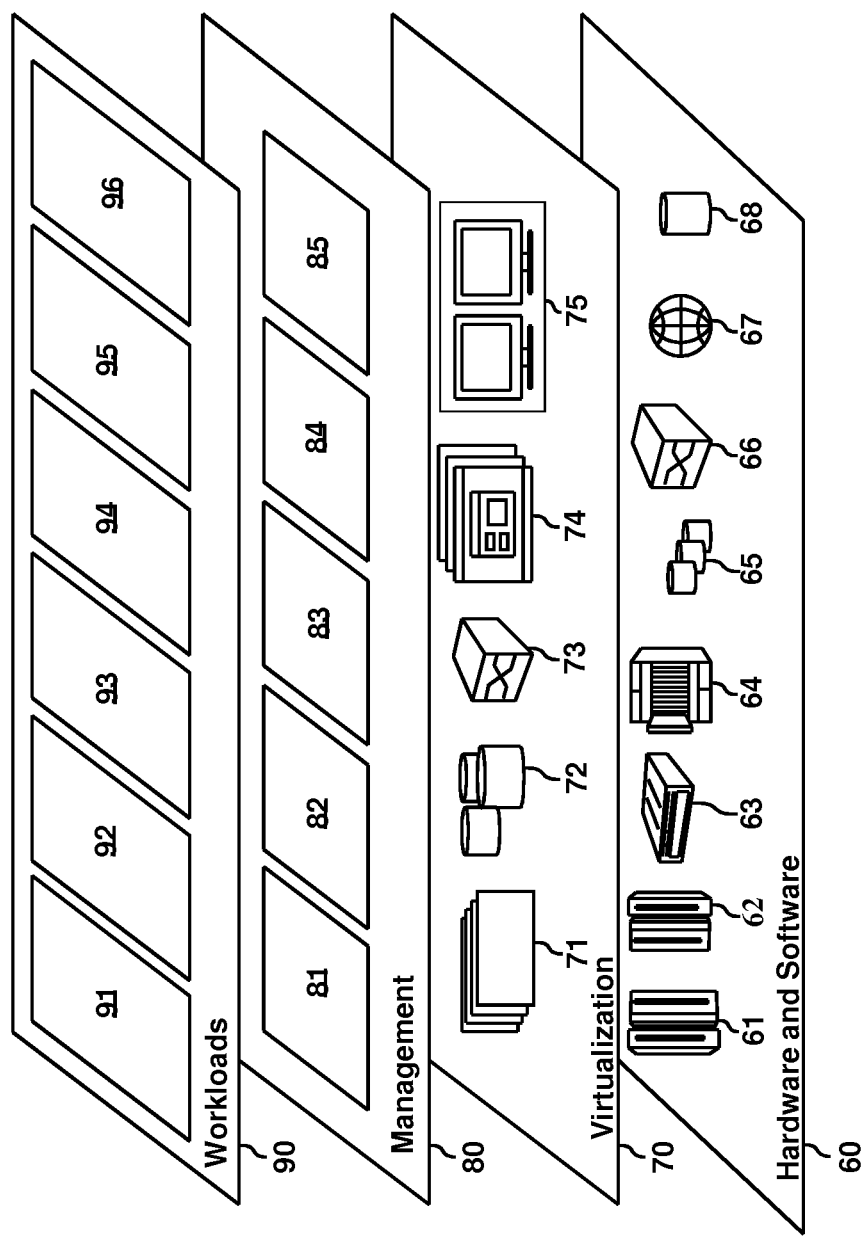
FIG. 5 depicts a set of functional abstraction layers provided in the cloud computing environment.

Referring now to FIG. 5, a set of functional abstraction layers provided by cloud computing environment 50 (FIG. 4) is shown. It should be understood in advance that the components, layers and functions shown in FIG. 5 are intended to be illustrative only and embodiments of the invention are not limited thereto. As depicted, the following layers and corresponding functions are provided.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and storage of applications for mobile devices 96.

The flowchart and block diagrams in the Figures illustrate the architecture, functionality and operation of possible implementations of systems, methods and computer program products according to various embodiments of the present invention. In this regard, each block in the flowchart or block diagrams may represent a module, segment, or portion of instructions which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method of evaluating information confidence based on cognitive behavior indicators of a user, the method comprising:
   determining, by a processor, a system generated answer to a question in an active learning question and answer system, wherein the system generated answer includes a first answer confidence score for the system generated answer;
   querying a user for an answer to the question in the active learning question and answer system based on the first answer confidence score;
   receiving, by the processor, information from the user as an answer to the question in the active learning question and answer system;
   monitoring, by the processor, the user for one or more cognitive behavior indicators when the user is providing the information, wherein the one or more cognitive behavior indicators comprise one or more biometric measurements of the user at a time the information is provided by the user and measures of an influence of an external stimuli on the user at the time the information is provided by the user;
   determining, by the processor, a second answer confidence score for the information received from the user based on the one or more biometric measurements of the user and the measures of the influence of an external stimuli on the user;
   annotating, by the processor, the information with the cognitive behavior indicators, a user profile associated with the user, and the second answer confidence score; and
   updating the first answer confidence score based at least in part on the second answer confidence score.

2. The computer-implemented method of claim 1, wherein the cognitive behavior indicator comprises a physiological measurement.

3. The computer-implemented method of claim 1, wherein the cognitive behavior indicator comprises one or more of user eye tracking, user typing speed, user heart rate, user breathing rate, user blink frequency, user skin conductance, electroencephalogram information, user body temperature, user perspiration quantity, user blood pressure and user amount of time elapsed during information input.

4. The computer-implemented method of claim 1, further comprising annotating the information, the cognitive trait and the second answer confidence score for the information received from the user with information received from cognitive behavior traits of other users.

5. The computer-implemented method of claim 1, further comprising excluding information from the user if the quantified level of the information confidence is below a designated threshold.

6. The computer-implemented method of claim 1, further comprising ranking results of the information and cognitive traits of multiple users based on the quantified level of information confidence.

7. The computer-implemented method of claim 1, wherein the cognitive behavior indicator is measured by a user-wearable device.

8. The computer-implemented method of claim 1, further comprising annotating the information with user characteristics stored in a user profile.

9. A system for evaluating information confidence based on cognitive behavior indicators of a user, the system comprising:
   a sensor to detect a cognitive behavior indicator of a user;
   a memory;
   a processor communicatively coupled to the memory and the sensor, where the processor is configured to perform:
      determine a system generated answer to a question in an active learning question and answer system, wherein the system generated answer includes a first answer confidence score for the system generated answer;
      querying a user for an answer to the question in the active learning question and answer system based on the first answer confidence score;
      receiving information from the user as an answer to a question in an active learning question and answer system;
      monitoring the user for one or more cognitive behavior indicator detected by the sensor when the user is providing the information, wherein the one or more cognitive behavior indicators comprise one or more biometric measurements of the user at a time the information is provided by the user and measures of an influence of an external stimuli on the user at the time the information is provided by the user;
      determining a second answer confidence score for the information received from the user based on the one or more biometric measurements fo the user and the measures of the influence of an external stimuli on the user; and
      annotating the information with the cognitive behavior indicators, a user profile associated with the user, and the second answer confidence score; and
   update the first answer confidence score based at least in part on the second answer confidence score.

10. The system of claim 9, wherein the cognitive behavior indicator comprises a physiological measurement.

11. The system of claim 9, wherein the cognitive behavior indicator comprises one or more of user eye tracking, user typing speed, user heart rate, user breathing rate, user blink frequency, user skin conductance, electroencephalogram information, user body temperature, user perspiration quantity, user blood pressure and user amount of time elapsed during information input.

12. The system of claim 9, wherein the processor is further configured to perform annotating the information, the cognitive trait and the second answer confidence score for the information received from the user with information received from cognitive behavior traits of other users.

13. A computer program product for evaluating information confidence based on cognitive behavior indicators of a user, the computer program product comprising:
   a computer readable storage medium having program instructions embodied therewith, wherein the computer readable storage medium is not a transitory signal per se, the program instructions executable by a processor to cause the processor to perform a method comprising:
      determining a system generated answer to a question in an active learning question and answer system, wherein the system generated answer includes a first answer confidence score for the system generated answer;
      querying a user for an answer to the question in the active learning question and answer system based on the first answer confidence score;

receiving information from the user as an answer to the question in the active learning question and answer system;

monitoring the user for one or more cognitive behavior indicators detected by a sensor when the user is providing the information, wherein the one or more cognitive behavior indicators comprise one or more biometric measurements of the user at a time the information is provided by the user and measures of an influence of an external stimuli on the user at the time the information is provided by the user;

determining a second answer confidence score for the information received from the user based on the one or more biometric measurements of the user and the measures of external stimuli on the user;

annotating the information with the cognitive behavior indicators, a user profile associated with the user, and the second answer confidence score; and updating the first answer confidence score based at least in part on the second answer confidence score.

14. The computer program product of claim 13, wherein the cognitive behavior indicator comprises a physiological measurement.

15. The computer program product of claim 13, wherein the cognitive behavior indicator comprises one or more of user eye tracking, user typing speed, user heart rate, user breathing rate, user blink frequency, user skin conductance, electroencephalogram information, user body temperature, user perspiration quantity, user blood pressure and user amount of time elapsed during information.

16. The computer program product of claim 13, wherein the computer readable program code is further configured to perform annotating the information, the cognitive trait and the second answer confidence score for the information received from the user with information received from cognitive behavior traits of other users.

17. The computer program product of claim 13, wherein the computer readable program code is further configured to perform excluding information from the user if the quantified level of the information confidence is below a designated threshold.

* * * * *